United States Patent [19]

Matay

[11] Patent Number: 4,545,249
[45] Date of Patent: Oct. 8, 1985

[54] ACOUSTICAL POSITION GAGE

[75] Inventor: Istvan M. Matay, No. Royalton, Ohio

[73] Assignee: TRW Inc., Cleveland, Ohio

[21] Appl. No.: 529,805

[22] Filed: Sep. 6, 1983

[51] Int. Cl.⁴ ............................................. G01N 29/04
[52] U.S. Cl. ........................................ 73/597; 73/609; 73/598; 367/125
[58] Field of Search .......................... 73/597, 609, 598; 367/125, 127

[56] References Cited

U.S. PATENT DOCUMENTS

| | | | |
|---|---|---|---|
| 3,121,955 | 2/1964 | King | 73/597 |
| 4,035,762 | 7/1977 | Chamuel | 73/609 |
| 4,144,574 | 3/1979 | Chamuel | 367/125 |
| 4,213,200 | 7/1980 | Matson, Jr. | 367/125 |
| 4,231,260 | 11/1980 | Chamuel | 73/597 |
| 4,241,430 | 12/1980 | Kayem et al. | 73/597 |

Primary Examiner—Howard A. Birmiel
Attorney, Agent, or Firm—Daniel G. Blackhurst

[57] ABSTRACT

An ultrasonic defect detection assembly (A) and an elongated workpiece (B) are mounted for relative movement. A mechanical assembly (C) provides relative movement between the workpiece and the examination assembly. An electronic circuit and display (D) produces a visual display indicating the relative position of the workpiece and the examination assembly, particularly the relative positions at which the examination assembly detects defects. A transmitting ultrasonic transducer (30) and a receiving ultrasonic transducer (38) are acoustically coupled with the workpiece, one being mounted at a preselected position on the workpiece and the other being mounted for relative movement with the examination assembly. The relative position of the workpiece and examination assembly is determined by measuring changes in a characteristic of the acoustic wave traveling between the transmitting and receiving transducers. In various alternate embodiments, the measured characteristic change includes travel time of the acoustic wave between the transmitting and receiving transducers, changes in the phase relationship between the acoustic wave at transmission and at monitoring, changes in the frequency of the acoustic wave when the frequency is adjusted to maintain the phase relationship substantially constant, and the like.

6 Claims, 5 Drawing Figures

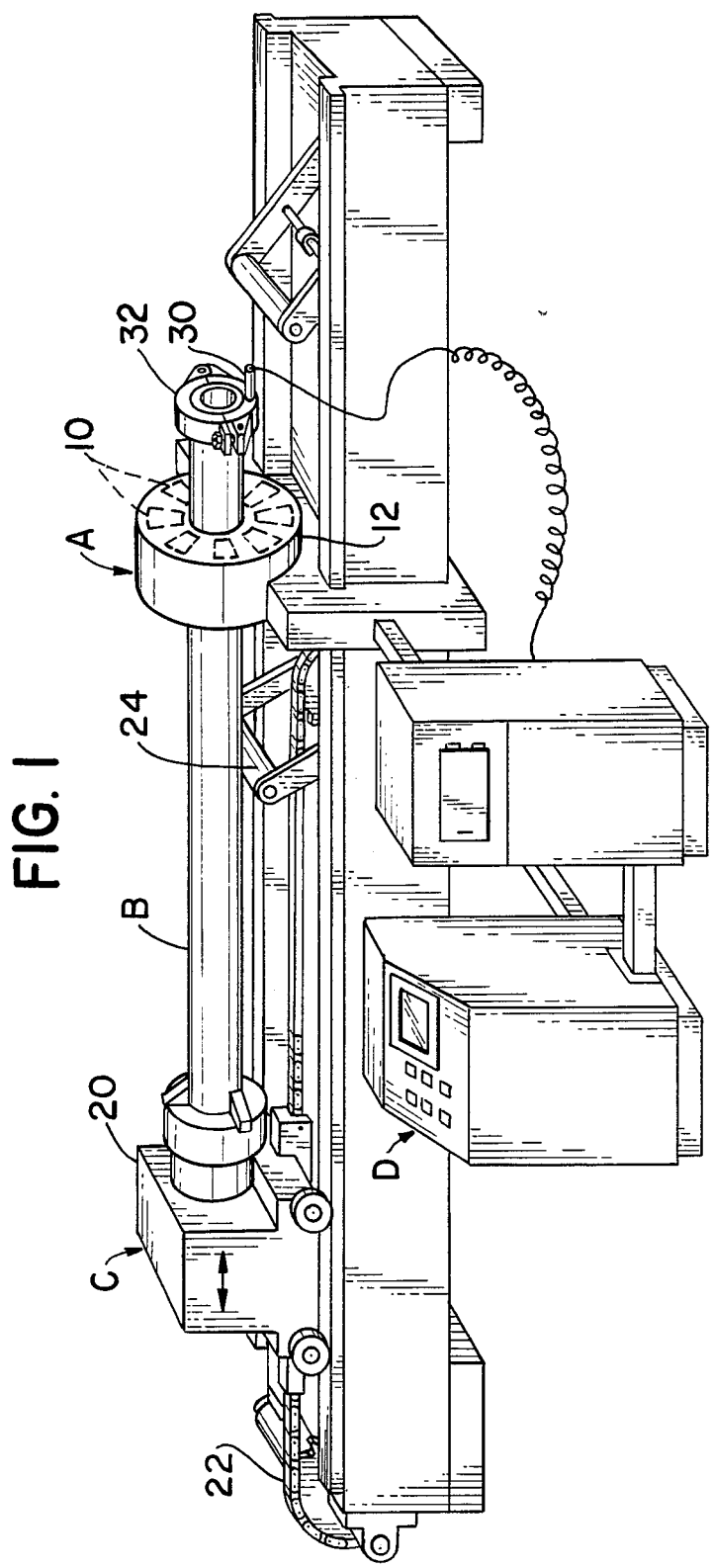

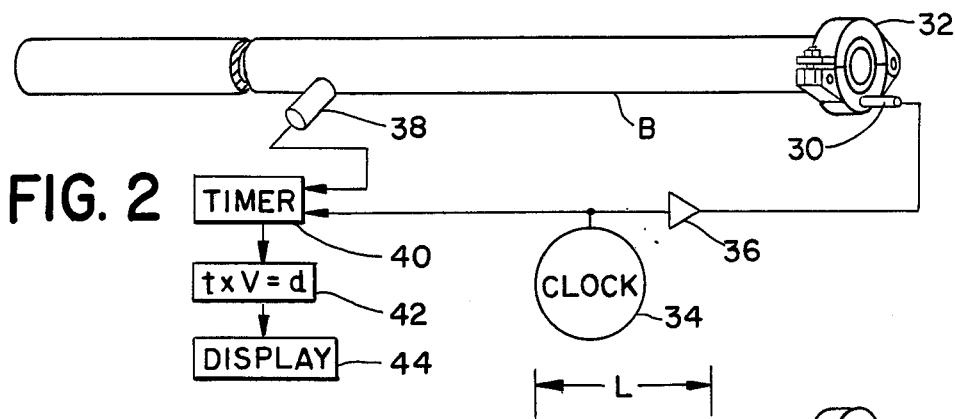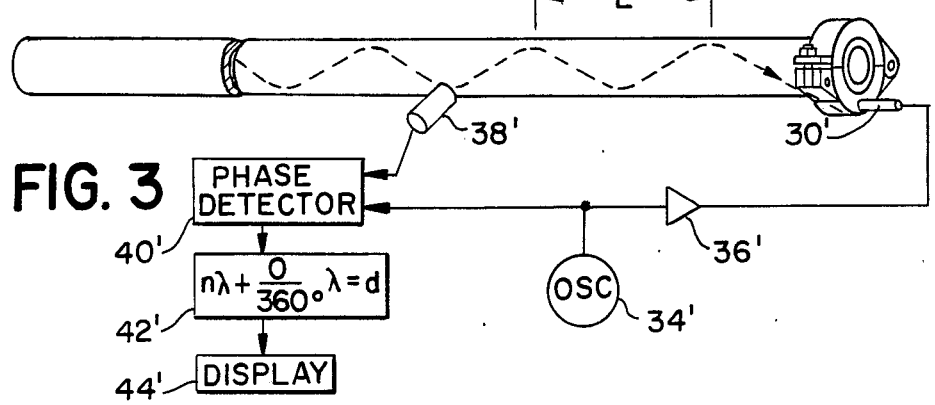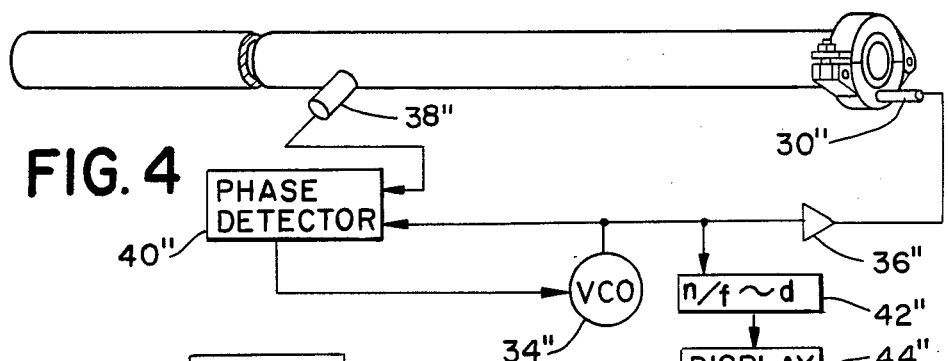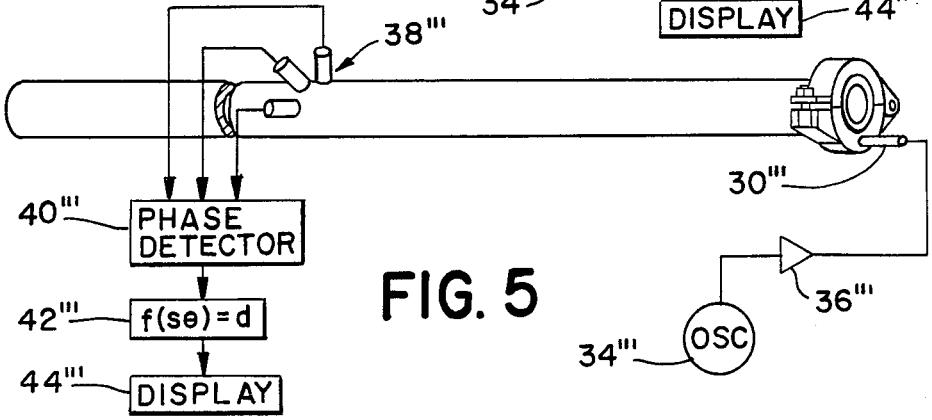

ACOUSTICAL POSITION GAGE

BACKGROUND OF THE INVENTION

The present invention relates to the art of acoustical measuring and gaging, particularly gaging the relative position of acoustically coupled objects as they undergo relative movement. The present invention finds particular application in gaging the relative position of an acoustical defect detection assembly and an elongated examined object, such as a metal pipe or tube, and will be described with particular reference thereto. It is to be appreciated, however, that the invention also finds utility in gaging the position of other acoustically coupled objects, such as a workpiece and an assembly for performing machining or drilling operations, a workpiece and an optical examination assembly, a robotic manipulation assembly and a guide track therefor, and the like.

Metal pipe and tubing of the type used in oil well drilling is commonly manufactured such that lengths in excess of 50 feet are routine. In well drilling, nuclear reactors, and other demanding installations, the tubular goods are commonly inspected at the point of use. Small defects, such as hairline cracks, can cause premature failure in an area which is not readily accessible for repair. These debilitating cracks commonly have dimensions as small as 10 mils (0.010 inches) or so. To locate this type of defect, the pipes may be inspected by means of an acoustical defect detection system. When the detection system locates a defect, the location of the defect must also be determined.

To be sure that defects or cracks of all orientations are located, it is common to examine the tubing a plurality of times, wherein a different mode of examination is employed each time. In order to determine whether two modes of examination are viewing the same defect or two closely adjacent defects, it is desirable to locate each defect with at least as fine a precision as the dimension of the flaw.

Heretofore, the relative position of the ultrasonic examination system and the workpiece was determined with a mechanical measurement system. These systems determine relative position by mechanically measuring various distances such as displacement of a cable for pulling a workpiece holder, rotational position of a rotating screw drive for the workpiece holder, rotation of workpiece supporting or engaging rollers, and the like. However, a measurement on the order of even 100 mils over a length of 50 feet would require precision on the order of a hundredth of a percent. Mechanical systems capable of measuring such long distances with this precision are unsuited to field installations.

The present invention contemplates new and improved method and apparatus which overcome the foregoing problems and others, and which facilitate measuring distances along a large or elongated object with high precision.

SUMMARY OF THE INVENTION

In accordance with the invention, a method of determining relative position of acoustically coupled objects undergoing relative movement is advantageously provided. An acoustic wave is transmitted from a transmission point and monitored at a monitoring point along one of the objects. One of the transmission and monitoring points is fixed relative to the one object and the other moves with the other object. A change in a characteristic of the acoustic wave is measured as the objects undergo relative movement. This change is correlated with relative position such that changes in the relative position or movement of the objects are acoustically measured.

The present invention encompasses several specific embodiments. In one embodiment, the measured characteristic comprises acoustic wave travel or propagation time. In another embodiment, the characteristic comprises acoustic wave phase. In further embodiments, yet other characteristics may be measured including frequency, phase variation or modulation, relative phase shift, angle of wave propagation, amplitude, and the like.

In accordance with another aspect of the invention, there is provided a method of determining the relative position of defects in a workpiece undergoing examination. The workpiece is moved relative to a workpiece acoustical examination assembly and an acoustic wave is transmitted along the workpiece from a transmission point to a monitoring point. One of the transmission and monitoring points is fixed relative to the workpiece and the other undergoes relative movement with the examination assembly. A change in a characteristic of the acoustic wave is measured as the workpiece and acoustic examination assembly undergo relative movement. This change is correlated with changes in relative position to produce an indication of the location of each detected defect.

In accordance with yet another aspect of the present invention, apparatus is provided for determining the relative position of defects in a workpiece. Here, an acoustic defect examination assembly is disposed to receive the workpiece in an acoustically coupled relationship therewith. Means are provided for causing relative movement between the workpiece and the acoustic examination assembly. An acoustic transmitting transducer is acoustically coupled to the workpiece at a transmission point, and a receiving transducer is acoustically coupled to the workpiece at a monitoring point. One of the transmitting and receiving transducers is fixedly connected with the workpiece, and the other is operatively connected with the examination assembly to undergo relative movement therewith. An electric circuit is connected with the transmitting transducer for causing it to generate at least one acoustic wave propagating along the workpiece. The electric circuit is further connected with the acoustic receiving transducer and produces an indication of the relative position defects as the workpiece and ultrasonic examination assembly undergo relative movement from a movement related change in a characteristic of the acoustic wave between the transmitting and receiving transducers.

A primary advantage of the present invention is in the provision of an arrangement for measuring relatively long distances with high precision.

Another advantage resides in the elimination of delicate electromechanical distance measuring devices.

Yet another advantage of the invention is that it utilizes the workpiece itself for distance measurement to eliminate design limitations imposed on scanning equipment by electromechanical position encoding devices.

Still further advantages and benefits of the invention will become apparent to those skilled in the art upon reading and understanding the following detailed description.

BRIEF DESCRIPTION OF THE DRAWINGS

The invention may take form in various steps and arrangements of steps or in various parts and arrangements of parts, preferred and alternative embodiments of which will be described in detail in this specification and illustrated in the accompanying drawings which form a part hereof and wherein:

FIG. 1 is a diagrammatic illustration of a system for acoustically measuring relative movement between a tubular workpiece and an ultrasonic examination assembly in accordance with the present invention;

FIG. 2 is a diagrammatic illustration of a circuit for measuring relative movement as a function of acoustic wave travel or propagation time;

FIG. 3 is a diagrammatic illustration of a circuit for measuring relative movement as a function of phase shift;

FIG. 4 is a diagrammatic illustration of a phase-locked loop relative position defecting circuit; and, FIG. 5 is a diagrammatic illustration of a circuit for acoustically interferometrically measuring relative position or movement.

DETAILED DESCRIPTION OF THE PREFERRED EMBODIMENT

Referring now to the drawings wherein the showings are for purposes of illustrating preferred and alternative embodiments of the invention only and not for purposes of limiting same, FIG. 1 shows an ultrasonic defect detection head assembly A disposed to receive an elongated workpiece B therethrough. A mechanical assembly C is provided for producing relative movement between the examination assembly and workpiece. An electronic circuit and display D produces a visual display indicating the position of detected defects along the workpiece, as well as an indication of the shape, size, orientation, and other physical aspects of the detected defects.

The acoustic examination assembly A includes a plurality of acoustic transducers 10 disposed in an acoustic coupling medium containing housing 12. The acoustic coupling medium, eg., water, acoustically connects the acoustic transducers and the workpiece. The acoustic transducers may be arranged at a variety of orientations and may be caused to transmit acoustic waves and receive acoustic echoes in various patterns as is known in the acoustical defect detection art.

The workpiece B, in the preferred embodiment, comprises a length of steel pipe, eg., a 50 foot length of eight inch diameter pipe. Other workpieces may similarly be examined by adjusting the arrangement of acoustical transducer and acoustical coupling medium to conform with one or more surfaces of the examined object. It is to be appreciated that the present invention may find utility in monitoring the relative position of a wide variety of pairs of objects, eg., an assembly for performing cutting, drilling, and like operations and a workpiece, a robotic manipulation assembly and a supporting guide track, and the like.

The mechanical positioning means C may comprise any one of numerous mechanical arrangements for moving the workpiece and the acoustical examining assembly relative to each other. In the illustrated embodiment, however, a workpiece supporting trolley generally designated 20 supports one end of the workpiece. A chain drive arrangement generally designated 22 selectively advances the trolley and the workpiece B.

A supporting means generally designated 24 supports the workpiece at a predetermined orientation adjacent the acoustical examining assembly. Optionally, the mechanical movement means may be arranged to move the workpiece through the acoustical examination assembly vertically or at other selected orientations.

The electronic control and display means D includes conventional electronic circuitry for controlling the transducers 10 of the acoustic head assembly A in accordance with prior art acoustical defect detection techniques. Further, the electronic circuit D includes a subcircuit for measuring change in a characteristic of an acoustic wave with relative movement. The change measuring circuit may take various forms in accordance with the characteristic chosen to be monitored, and specific embodiments thereof in accordance with the subject invention will be described with reference to FIGS. 2-5.

With particular reference to FIG. 2, the measured characteristic comprises acoustic wave travel or propagation time. The change measuring circuit includes a transmitting acoustic transmitter or transducer 30, which as illustrated in FIG. 1, is fixedly mounted by an acoustic coupling medium containing collar 32 adjacent one end of the workpiece. The position of the transmitting transducer at one end of the workpiece is a reference point or origin relative to which movement and relative position between the workpiece and examination assembly is measured.

Referring again to FIG. 2, a clock 34 periodically causes a triggering amplifier 36 to trigger the transmitting transducer 30 to generate an acoustic wave traveling axially along the workpiece. A receiving acoustic transducer 38 is disposed in the housing 12 in an acoustically coupled relationship with the workpiece to monitor the axially transmitted acoustic wave from transducer 30. Because the direction of propagation plays no part in the distance calculation, the transmitting and receiving transducers may be reversed. A counter timer 40 is connected with the receiving transducer and the clock to measure the time interval between transmission and receipt of the axially transmitted acoustic wave. A correlating means 42 produces an indication of distance between the transmitting and receiving transducers.

Specific to this embodiment, the correlating means multiplies the transmission time interval by the propagation velocity of the acoustic wave in the workpiece and by a constant which is appropriate to selected engineering units. The propagation velocity may be measured experimentally, may be calculated mathematically, or may be determined by a combination of the two. As the workpiece and the acoustical examination assembly move relative to each other, changes in the propagation time are indicative of relative movement therebetween. A display means 44 displays the relative distance or displacement in the selected engineering units.

The relative distance or displacement is monitored and recorded each time the transducer array 10 detects a defect. This provides a record of the axial location of each defect relative to the reference point or origin, ie., the end of the workpiece where transducer 30 is mounted. Further, the defect locations are determined to a fraction of the wave length of the acoustic wave. This same type of process may advantageously be employed with the various alternative circuits described hereinafter.

FIG. 3 illustrates an alternate embodiment of a change measuring circuit in which the changing characteristic comprises the phase of the transmitted acoustic wave. FIG. 3, like components of the embodiment of FIG. 2 are identified by like numerals with a primed (') suffix. A transmitting transducer 30' is driven at a fixed frequency by an oscillator 34' and amplifier 36'. In a relative uniform medium such as the steel workpiece, a wave (illustrated in phantom) with a fixed frequency has a corresponding fixed wave length L. A receiving transducer 38' in the housing 12 monitors the acoustic wave. A phase detector 40' is connected with the oscillator 34' and the receiving transducer 38' to detect the relative phase of the transmitted and received waves.

Each time the transmitting and receiving transducers move relative to each other, the phase of the transmitted and received acoustic wave shifts correspondingly. Specifically, relative movement of a distance equal to the wave length of the acoustic wave produces a phase shift of 360°. Analogously, a 90° phase shift corresponds to movement by a quarter of the wave length, a 180° phase shift corresponds to movement by half the wave length, and so forth. A correlating means 42' counts the number of full wave lengths between the transmitting and receiving transducers and determines a fractional wave length from the phase difference detected by the phase detector 40'.

More specifically, the correlating means multiplies the number and fractional wave cycles by the experimentally measured or calculated wave length and a constant appropriate to selected engineering units to be displayed. Preferably, the acoustic transmitted wave has a relatively low frequency and long wave length. The low acoustic frequency keeps the gaging acoustic wave from interfering with the defect detection acoustic waves which are typically in the ultrasonic range. On the other hand, the longer the wave length, the longer the relative movement which corresponds to each degree of phase shift. Thus, there is a trade off between the wave length, the precision of measurement, and the precision of the phase detector. A display means 44' displays the relative distance or displacement in the selected engineering units.

FIG. 4 illustrates another alternate embodiment of the displacement measurement circuit. In FIG. 4, like components are identified by like numerals with a double primed ('') suffix. A voltage controlled oscillator 34'' and an amplifier 36'' drive a transmitting transducer 30''. A phase detector 40'' is connected with a receiving transducer 38'' and the voltage oscillator 34'' to compare the phase of the transmitted and the received signals. The phase detector produces an output voltage which varies with the difference in the phases of the two signals. The voltage signal is applied to the voltage controlled oscillator 34'' to vary its frequency in proportion with a detected phase difference. In this manner, the frequency of the oscillator 34'' is adjusted such that the transmitting and receiving transducers remain a fixed number of wave lengths apart.

However, the size of the wave length, ie., the frequency, varies in proportion to relative movement. A correlating means 42'' transforms the frequency of the voltage controlled oscillator into an indication of the relative distance between the transmitting and receiving transducers. The distance is proportional to the fixed number of cycles multiplied by the inverse of frequency, ie., wave length. Optionally, the correlating means may monitor the frequency of the oscillation by monitoring the control voltage from the phase detector. A display means 44'' displays the relative distance in selected engineering units.

FIG. 5 illustrates still another alternate embodiment of the change measuring circuit of the present invention. In FIG. 5, like components are identified by the like numerals followed by a triple primed (''') suffix. An oscillator 34''' and amplifier 36''' drive a transmitting transducer 30''' at a fixed frequency. A plurality or array of receiving transducers 38''' are disposed axially offset and at an angle to the transmitting transducer. In the illustrated embodiment of FIG. 5, the receiving transducer array is disposed approximately 180° from the transmitting transducer and perpendicular to the axial direction. In this manner, acoustic waves from the transmitting transducer impinge upon the receiving array at an angle which varies with displacement. Because the waves are received at an angle, there is a phase shift between each receiving transducer of the array.

A phase detector 40''' detects the relative phase difference between the received wave at each of the transducers of the array. A correlating means 42''' first determines the angle at which the acoustic wave impinged upon the array from the phase difference. Second, the display means trigonometrically calculates the distance between the transmitting transducer and the receiving array. This calculation is made from the peripheral displacement between the transmitting receiver and receiving array and the angle of incidence. A display mans 44''' displays the relative distance.

As yet another alternative, a transmitting array may be provided with a phase adjusting means such that the array is capable of transmitting the acoustic wave at a selected angle. At the start of the examination, the transmitted ultrasonic wave is aimed at a receiving transducer. A peak signal detector connected with the receiving transducer causes the phase controller to adjust the phase between the transducers of the transmitting array such that the transmitted wave remains aimed at the receiving transducers as they move apart. From the relative phase of the phase controller, the distance between the transmitting and receiving transducers is again trigonometrically calculable.

As another option, the transmitting array may be focused such that transmitted waves add to produce a peak or subtract to produce a null at a selected distance or focal point. The focus, ie., the distance to the focal point, is adjusted to maintain the focal point coincident with the receiving transducer.

As yet another alternative, the phase lock-loop detection system of FIG. 4 may be used in conjunction with a pulse compressed chirped wave. The signal is frequency swept and compressed in time to produce a relatively narrow pulse or chirp signal.

The invention has been described with reference to preferred and alternate embodiments. Obviously, modifications and alterations will occur to others upon reading and understanding this specification. It is intended to include all such modifications and alterations insofar as they come within the scope of the appended claims or the equivalents thereof.

Having thus described the invention, it is now claimed:

1. A method of determining a relative position of acoustically coupled objects including a workpiece undergoing relative movement, the method comprising:
   transmitting an acoustic wave from a transmission point along one of the objects;

monitoring the acoustic wave at a monitoring point along the one object, one of the transmission and monitoring points being at a preselected point on the one object and the other of the transmission and monitoring points being movable in a fixed relationship to the other object;

measuring the rate of propagation of said acoustic wave through the workpiece relative to the movement of the objects; and, correlating the change in the rate of propagation with relative position of the objects, whereby changes in the relative position of the objects are acoustically measured.

2. A method of determining relative positions of defects in a workpiece undergoing examination, the method comprising:

moving a workpiece and an examination assembly relative to each other;

transmitting an acoustic wave along the workpiece;

monitoring the acoustic wave adjacent the examination assembly;

performing one of the acoustic wave transmitting and acoustic wave monitoring steps at a preselected reference point along the workpiece;

performing the other of the acoustic wave transmitting and acoustic wave monitoring steps adjacent the examination assembly;

examining the workpiece with high frequency ultrasonic waves for defects, said acoustic wave being in a frequency range which does not interfere with the ultrasonic examination;

upon observing a defect, measuring the rate of propagation of said acoustic wave along the workpiece between transmission and monitoring; and, correlating the characteristic change with the relative position of the workpiece and examination assembly, whereby the relative position of defects along the workpiece is acoustically measured.

3. An apparatus for determining the relative position of acoustically coupled objects which undergo relative movement, the apparatus comprising:

first and second acoustically coupled objects disposed to undergo relative movement therebetween;

means for causing the first and second objects to undergo relative movement;

an acoustic wave transmitting transducer acoustically coupled with the first object for transmitting an acoustic wave therealong;

a receiving acoustic transducer acoustically coupled with the first object for monitoring the acoustic wave transmitted by the transmitting transducer;

one of the transmitting and receiving transducers being coupled to the first object at a preselected reference point and the other of the transmitting and receiving transducers being operatively connected with the second object in a preselected relationship therewith;

electrical circuit means operatively connected with the transmitting and receiving transducers, said circuit means including;

clock means for periodically causing the transmitting transducer to generate an acoustic wave traveling along the first object;

timing means for timing a time interval between transmissions of the acoustic wave by the transmitting transducer and monitoring the acoustic wave by the receiving transducer, the timing means being operatively connected with the receiving transducer and the clock means;

correlating means operatively connected with the timing means for correlating the timed interval with the relative position of the objects, whereby the relative position of said receiving and transmitting transducers is determined.

4. An apparatus for determining the relative position of acoustically coupled objects which undergo relative movement, the apparatus comprising:

first and second acoustically coupled objects disposed to undergo relative movement therebetween;

means for causing the first and second objects to undergo relative movement;

an acoustic wave transmitting transducer acoustically coupled to the first object for transmitting an acoustic wave therealong;

a receiving acoustic transducer acoustically coupled with the first object for monitoring the acoustic wave transmitted by the transmitting transducer;

one of the transmitting and receiving transducers being coupled to the first object at a preselected reference point and the other of the transmitting and receiving transducers being operatively connected with the second object in a preselected relationship therewith;

electric circuit means operatively connected with the transmitting and receiving transducers for determining the relative position thereof, said electrical circuit including voltage controlled oscillator means operatively connected with the transmitting transducer for causing the transmitting transducer to transmit an ultrasonic wave at a given oscillator frequency;

phase detection means operatively connected with the oscillator means and the receiving transducer said phase detection means for measuring a difference in the phase of the acoustic wave at transmission by the transmission transducer and at monitoring by the receiving transducer, said phase detector being adapted to produce an output voltage which varies in proportion to said detected phase difference, the output voltage being operatively connected with the voltage controlled oscillator such that the oscillation frequency is varied in a manner which maintains the detected phase substantially constant; and, correlating means operatively connected to the voltage controlled oscillator for correlating the oscillation frequency with the relative position of the objects.

5. The apparatus as set forth in claim 4 wherein the first object comprises an elongated tube and the second object comprises an ultrasonic examination assembly which is acoustically coupled with the tubular object to examine for defects therein.

6. A method of determining relative positions of defects in a workpiece undergoing examination, the method comprising:

moving a workpiece and an examination assembly relative to each other; transmitting an acoustic wave along the workpiece; monitoring the acoustic wave adjacent the examination assembly;

performing one of the acoustic wave transmitting and acoustic wave monitoring steps at a preselected reference point along the workpiece;

performing the other of the acoustic wave transmitting and acoustic wave monitoring steps adjacent the examination assembly; examining the workpiece with high frequency ultrasonic waves for defects, said acoustic wave being in a frequency range that does not interfere with the ultrasonic examination; upon observing a defect measuring a change between the acoustic wave at transmission and at monitoring, said measuring step including adjusting the frequency at which the acoustic wave is transmitted in response to the detected phase relationship changes in such a manner that a substantially constant phase relationship is maintained between the acoustic wave at transmission and monitoring; and correlating the characteristic change in the transmission frequency with changes in the relative position.

* * * * *